US 6,579,916 B1

(12) United States Patent
Askill et al.

(10) Patent No.: US 6,579,916 B1
(45) Date of Patent: Jun. 17, 2003

(54) METHODS FOR STERILIZING CYANOACRYLATE COMPOSITIONS

(75) Inventors: Ian N. Askill, Colorado Springs, CO (US); Shane C. Karnik, Gales Ferry, CT (US); Richard L. Norton, Fort Collins, CO (US)

(73) Assignee: MedLogic Global Corporation, Devon (GB)

( * ) Notice: Subject to any disclaimer, the term of this patent is extended or adjusted under 35 U.S.C. 154(b) by 0 days.

(21) Appl. No.: 09/989,752

(22) Filed: Nov. 21, 2001

Related U.S. Application Data

(60) Provisional application No. 60/252,832, filed on Nov. 21, 2000.

(51) Int. Cl.$^7$ .............................. C08F 21/46; C08F 2/48; C08K 3/28
(52) U.S. Cl. ....................... 522/152; 522/153; 522/1; 522/173; 522/79; 522/74; 522/181; 523/111; 523/118; 422/1; 422/22; 514/527; 524/296; 524/297
(58) Field of Search ............................ 522/1, 152, 153, 522/173, 79, 74, 181; 422/1, 22; 514/527; 523/111, 118; 524/296, 297

(56) References Cited

U.S. PATENT DOCUMENTS

| | | |
|---|---|---|
| 2,784,127 A | 3/1957 | Joyner et al. |
| 3,527,224 A | 9/1970 | Rabinowitz |
| 3,591,676 A | 7/1971 | Hawkins et al. |
| 3,654,239 A | 4/1972 | McIntire et al. |
| 3,667,472 A | 6/1972 | Halpern |
| 3,995,641 A | 12/1976 | Kronenthal et al. |
| 4,035,334 A | 7/1977 | Davydov et al. |
| 4,038,345 A | 7/1977 | O'Sullivan et al. |
| 4,444,933 A | 4/1984 | Columbus et al. |
| 4,650,826 A | 3/1987 | Waniczek et al. |
| 4,652,763 A | 3/1987 | Nablo |
| 5,254,132 A | 10/1993 | Barley et al. |
| 5,258,423 A | 11/1993 | Crabb et al. |
| 5,480,935 A | 1/1996 | Greff et al. |
| 5,496,302 A | 3/1996 | Minshall et al. |
| 5,530,037 A | 6/1996 | McDonnell et al. |
| 5,653,769 A | 8/1997 | Barley et al. |
| 5,684,042 A | 11/1997 | Greff et al. |
| 5,730,994 A | 3/1998 | Askill et al. |
| 5,874,044 A | 2/1999 | Kotzev |
| 5,998,472 A | 12/1999 | Berger et al. |
| 6,055,828 A * | 5/2000 | Rivera et al. ................ 422/21 |
| 6,143,805 A | 11/2000 | Hickey et al. |
| 6,248,800 B1 | 6/2001 | Greff et al. |
| 6,310,166 B1 | 10/2001 | Hickey et al. |

FOREIGN PATENT DOCUMENTS

| | | |
|---|---|---|
| GB | 1281457 | 7/1972 |
| GB | 2306469 | 5/1997 |
| WO | WO 93/25196 | 12/1993 |
| WO | WO 00/16615 | 3/2000 |

* cited by examiner

Primary Examiner—James J. Seidleck
Assistant Examiner—Sanza L. McClendon
(74) Attorney, Agent, or Firm—Burns, Doane, Swecker & Mathis L.L.P.

(57) ABSTRACT

Disclosed are methods for sterilizing cyanoacrylate prepolymer compositions under visible light irradiation conditions wherein the prepolymer remains in polymerizable form after sterilization.

15 Claims, No Drawings

METHODS FOR STERILIZING CYANOACRYLATE COMPOSITIONS

CROSS-REFERENCE TO RELATED APPLICATIONS

This application claims the benefit of U.S. Provisional Patent Application Serial No. 60/252,832 filed Nov. 21, 2000 which application is incorporated herein by reference in its entirety.

BACKGROUND OF THE INVENTION

FIELD OF THE INVENTION

This invention is directed to methods for sterilizing cyanoacrylate propolymer compositions under conditions wherein the prepolymer remains in polymerizable (non-gelled) form after sterilization. The methods of this invention employ, in part, visible light irradiation sterilization techniques.

REFERENCES

The following patent applications and patents are cited and/or referenced in this application as superscript numbers:

[1] Hawkins, et al., Surgical Adhesive Compositions, U.S. Pat. No. 3,591,676, issued on Jul. 6, 1971
[2] Halpern, et al., Adhesive for Living Tissue, U.S. Pat. No. 3,667,472, issued on Jun. 6, 1972
[3] McIntire, et al., Process for the Preparation of Poly(α-Cyanoacrylates), U.S. Pat. No. 3,654,239, issued on Apr. 4, 1972
[4] Barley, et al., Methods for Treating Non-Suturable Wounds by Use of Cyanoacrylate Adhesives, International Patent Application Publication No. WO 93/25196, published on Dec. 23, 1993
[5] Barley, et al., Methods for Treating Suturable Wounds by Use of Sutures and Cyanoacrylate Adhesives, U.S. Pat. No. 5,254,132, issued on Oct. 19, 1993
[6] Barley, et al., Methods for Reducing Skin Irritation From Artificial Devices by Use of Cyanoacrylate Adhesives, U.S. Pat. No. 5,653,769, issued on Aug. 5, 1997
[7] Rabinowitz, et al., Method of Surgically Bonding Tissue Together, U.S. Pat. No. 3,527,224, issued on Sep. 8, 1970
[8] Kronenthal, et al., Surgical Adhesives, U.S. Pat. No. 3,995,641, issued on Dec. 7, 1976
[9] Davydov, et al., Medical Adhesive, U.S. Pat. No. 4,035,334, issued on Jul. 12, 1977
[10] Waniczek, et al., Stabilized Cyanoacrylate Adhesives Containing Bis-Trialkylsilyl Esters of Sulfuric Acid, U.S. Pat. No. 4,650,826, issued on Mar. 17, 1987
[11] Askill, et al., "Methods for Draping Surgical Incision Sites" U.S. Pat. No. 5,730,994 issued on Mar. 24, 1998
[12] Stehlik, "Sterilisation of Tissue Binding Adhesives", British Patent Application Publication No. 1 281 457, published on Jul. 12, 1972
[13] McDonnell, et al., "Sterilized Cyanoacrylate Adhesive Composition, and a Method of Making Such a Composition", U.S. Pat. No. 5,530,037, issued on Jun. 25, 1996
[14] Greff, et al., "Cyanoacrylate Adhesive Compositions", U.S. Pat. No. 5,480,935, issued on Jan. 2, 1996
[15] Askill, et al., "Package for Cyanoacrylate Composition", U.S. patent application Ser. No.09/062,514, filed on Apr. 17, 1997
[16] O'Sullivan, et al., High Viscosity Cyanoacrylate Adhesive Compositions, and Process for Their Preparation, U.S. Pat. No. 4,038,345, issued on Jul. 26, 1977
[17] Joyner, et al., Plasticized Monomeric Adhesive Compositions and Articles Prepared Therefrom, U.S. Pat. No. 2,784,127, issued on Mar. 5, 1957
[18] Columbus, et al., Adhesive Cyanoacrylate Compositions with Reduced Adhesion to Skin, U.S. Pat. No. 4,444,933, issued on Apr. 24, 1984
[19] Greff, et al., "Cyanoacrylate Compositions Comprising an Antimicrobial Agent", U.S. Pat. No. 5,684,042, issued on Nov. 4, 1997
[20] Kotsev, British Patent Application Serial No. 2 306 469A, "Sterilizing Cyanoacrylate Preparations" published May 7, 1997
[21] Greff, et al., U.S. Pat. No. 6,248,800, Methods for Sterilizing Cyanoacrylate Compositions, issued on Jun. 19, 2001
[22] Hickey, et al., U.S. Pat. No. 6,143,805, Electron Beam Sterilization of Liquid Adhesive Compositions, issued on Nov. 7, 2000

All of the above patent applications and patents are herein incorporated by reference in their entirety to the same extent as if each individual patent application or patent was specifically and individually indicated to be incorporated by reference in its entirety.

STATE OF THE ART

Compositions comprising cyanoacrylate esters have been disclosed as having adhesive properties suitable for a variety of human medical uses. Such uses include, for example, use as a replacement or adjunct for sutures or staples in closing the dermal layer of an incision after surgery; use as a hemostat; use in covering small non-suturable wounds on skin surfaces; use in inhibiting surface skin irritation arising from friction between the skin surface and artificial devices such as tapes, prosthetic devices, casts, etc.; and use in the in situ formation of a surgical incise drape.[1-6, 11]

In each case, when topically applied to mammalian skin, the cyanoacrylate rapidly polymerizes, typically within a minute, to form a coherent, adhesive, polymeric film which strongly adheres to the skin.

Cyanoacrylate esters suggested for such uses include the following structures:

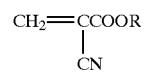

wherein R is an alkyl or other suitable substituent. Such cyanoacrylate esters are disclosed in, for example, U.S. Pat. Nos. 3,527,224; 3,591,676; 3,667,472; 3,995,641; 4,035,334; and 4,650,826.[1,2,7-10]

In view of the numerous medical uses of cyanoacrylate ester compositions, sterilized forms of these compositions would be particularly beneficial. In fact, it would be particularly desirable if the sterilization techniques were conducted on the packaged product so that, upon sterilization, the sterilized composition could be immediately shipped. Sterilization of the packaged product would thereby prevent reintroduction of microbial contaminants during the packaging step.

However, when applied to cyanoacrylate ester compositions, conventional sterilization techniques are often unsuitable or suffer from undesirable results. For example, it is essential that the selected sterilization technique employed does not cause in polymerization of the cyanoacrylate ester and, accordingly, high temperature heat or steam sterilization techniques are often contra-indicated, although Dimiter[20] reports the use of heat sterilization temperatures of at least 160° C. for these compositions. Similarly, when sterilization is conducted on packaged cyanoacrylate ester compositions, selected sterilization methods must be able to penetrate the packaging material and sterilize the entire contents of the package including the cyanoacrylate ester composition.

In point of fact, Stehlik[12] recites that normal sterilization processes such as steam-sterilization, heat sterilization, gas treatment, sterile filtration and ionizing radiation at room temperature are unacceptable because these processes result in polymerization of the cyanoacrylate ester leading to solid compositions unsuitable for use as adhesives. Stehlik goes on to disclose that sterilization of cyanoacrylate compositions can be preferably achieved by first solidifying the composition by freezing the composition at very low temperatures (−196° C. and 80° C. being disclosed in the examples) and then exposing the frozen, solidified composition to γ-ionizing radiation. In this reference, radiation doses of, e.g., 1.5 mRad of $Co^{60}$ γ-radiation, were disclosed as killing bacterial spores.

It is apparent, however, that the use of low temperatures to achieve solidification of the cyanoacrylate ester composition is not practical for manufacture on an industrial scale.

McDonnell, et al.[13] also recite that most sterilization methods are unsuitable or suffer severe limitations in their applicability to cyanoacrylate compositions and, in particular, packaged cyanoacrylate compositions. In fact, this reference discloses that sterilization via electron beam (E-beam) exposure is unacceptable because E-beam accelerators have relatively low penetrating ability and would be effective only in sterilizing the outer surfaces of the package. McDonnell, et al. then recites sterilization techniques using a very high dose of γ-irradiation (at least 2.5 mRad) delivered to the composition at room temperature.

Notwithstanding McDonnell, et al.'s disclosure, several references disclose successful sterilization of cyanoacrylates using E-beam techniques. See, for example, Greff, et al.[21] and Hickey, et al.[22]

However, E-beam sterilization techniques require specialized instrumentation which is very expensive and has limits on its penetrating abilities as described by Greff, et al.[21] Moreover, installation and operation of such instrumentation is neither practical not cost effective for most manufacturing companies. Devises sterilized by E-beam are typically shipped away to a dedicated facility leading to significant cost and production delays. Accordingly, more accessible and cost effective techniques for cyanoacrylate sterilization would be beneficial.

SUMMARY OF THE INVENTION

This invention is directed to methods for sterilizing cyanoacrylate ester compositions. In particular, this invention is directed to the novel and unexpected result that, under carefully controlled conditions, cyanoacrylate ester compositions can be sterilized using visible light irradiation at room temperature conditions.

In a particular aspect, it has been discovered that employing a sufficiently energetic visible light source allows for sterilization of polymerizable cyanoacrylate ester compositions without significant polymerization of these compositions.

Accordingly, in one of its method aspects, this invention is directed to a method for preparing a polymerizable, sterile, cyanoacrylate ester composition wherein the method comprises exposing a polymerizable cyanoacrylate ester composition to a sufficient dosage of visible light irradiation under conditions wherein the cyanoacrylate ester composition is sterilized without gelling the composition.

In a preferred embodiment, the polymerizable cyanoacrylate ester is a polymerizable monomer or reactive oligomer of a cyanoacrylate ester. Such monomers and reactive oligomers are sometimes referred to herein simply as "prepolymers" and, in monomeric form, are preferably represented by formula I:

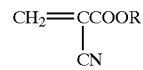

wherein R is selected from the group consisting of:
  alkyl of 1 to 10 carbon atoms,
  alkenyl of 2 to 10 carbon atoms,
  cycloalkyl groups of from 5 to 8 carbon atoms,
  phenyl,
  2-ethoxyethyl,
  3-methoxybutyl,
  and a substituent of the formula:

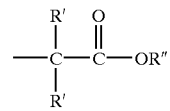

wherein each R' is independently selected from the
    group consisting of:
    hydrogen and methyl, and
  R" is selected from the group consisting of:
    alkyl of from 1 to 6 carbon atoms,
    alkenyl of from 2 to 6 carbon atoms,
    alkynyl of from 2 to 6 carbon atoms,
    cycloalkyl of from 3 to 8 carbon atoms,
    aralkyl selected from the group consisting of benzyl,
      methylbenzyl and phenylethyl,
    phenyl, and
    phenyl substituted with 1 to 3 substituents selected
      from the group consisting of hydroxy, chloro,
      bromo, nitro, alkyl of 1 to 4 carbon atoms, and
      alkoxy of from 1 to 4 carbon atoms.

More preferably, in the cyanoacrylate esters of formula I, R is alkyl of from 2 to 10 carbon atoms and still more preferably alkyl of from 4 to 8 carbon atoms. Even more preferably, R is butyl, pentyl or octyl and most preferably, R is n-butyl.

In another preferred embodiment, the cyanoacrylate ester composition is formulated to contain an effective amount of a mixture of a biocompatible acid polymerization inhibitor and a biocompatible free radical polymerization inhibitor to inhibit polymerization of the cyanoacrylate ester and an effective amount of a biocompatible plasticizer.

The preferred mixture of polymerization inhibitors is a biocompatible acid polymerization inhibitor such as sulfur dioxide, glacial acid and other well known acid polymerization inhibitors and a biocompatible free radical polymerization inhibitor including hydroquinone and hindered phenols (e.g., 4-methoxyphenol). The acid polymerization inhibitor is preferably $SO_2$ which is preferably employed at from about 50 to 1000 ppm, more preferably from about 50 to 500 ppm, and even more preferably from about 200 to 500 ppm, based on the total weight of the composition. The free radical inhibitor is preferably hydroquinone which is preferably employed at a concentration of from about 50 to 250 ppm and more preferably at about 150 ppm. In a particularly preferred embodiment, the polymerization inhibitor is selected such that it does not form decomposition products on exposure to visible light irradiation which are toxic or irritating to mammalian skin or which cause premature polymerization or prevent the polymerization of the cyanoacrylate ester composition.

Preferred biocompatible plasticizers are dioctyl phthalate and/or acetyl tri-n-butyl citrate which are employed in sufficient amounts to enhance the flexibility of the resulting polymeric cyanoacrylate film. Again, in a particularly preferred embodiment, the biocompatible plasticizer is selected such that it does not form decomposition products on exposure to visible light irradiation which are toxic or irritating to mammalian skin or which cause premature polymerization or prevent the polymerization of the cyanoacrylate ester composition.

In another preferred embodiment, the cyanoacrylate ester composition further comprises a compatible antimicrobial agent and even more preferably an antimicrobial complex of iodine molecules with a biocompatible polymer. Such complexes include the commercially available povidone iodine which can be mixed with the cyanoacrylate composition prior to visible light sterilization or can be included as a separate component (e.g., a two component system) in the packaged cyanoacrylate composition wherein the cyanoacrylate component is sterilized by visible light irradiation.

The methods of this invention are particularly beneficial when the cyanoacrylate composition to be sterilized is in a packaging element. In this aspect, this invention is directed to a method for preparing a polymerizable, sterile, cyanoacrylate ester composition in a packaging element wherein the method comprises:

(a) selecting a packaging element which is transparent to visible light irradiation;

(b) adding a cyanoacrylate ester composition to the packaging element selected in (a) above; and (c) exposing the packaging element formed in (b) above to a sufficient dosage of visible light irradiation to sterilize both the packaging element and the cyanoacrylate ester composition therein without gelling the composition.

In still another of its method aspects, this invention is directed to a method for preparing a polymerizable, sterile, cyanoacrylate ester composition in a packaging element wherein the method comprises:

(a) selecting a packaging element in the form of an ampule having a neck portion configured for heat sealing after fill wherein said packaging element is transparent to visible light irradiation;

(b) exposing said ampule to a sufficient amount of a sanitizing agent to reduce the level of bioburden on the ampule;

(c) selecting a polymerizable cyanoacrylate ester composition;

(d) filtering said cyanoacrylate ester composition through a biofilter having a maximum pore size of less than about 1 micron;

(e) adding the filtered cyanoacrylate ester composition to the ampule prepared in (b) above;

(f) sealing the ampule prepared in (e) by heat sealing the neck portion of said ampule;

(g) combining ampules produced in (f) above into a set of ampules;

(h) sealing the set of ampules formed in (g) above with a secondary sealing means so as to form a packaging element comprising said set of ampules; and (i) exposing the packaging element formed in (h) above to a sufficient dosage of visible light to sterilize both the packaging element and the cyanoacrylate ester composition therein without solidifying or gelling the composition.

Preferred sanitizing agents include, for example, heat, plasma and ethylene oxide gas.

DETAILED DESCRIPTION OF THE PREFERRED EMBODIMENTS

This invention is directed, in part, to methods for sterilizing cyanoacrylate prepolymer compositions with visible light irradiation wherein the prepolymer remains in polymerizable, non-gelled form after sterilization. Prior to describing this invention in further detail, the following terms will first be defined.

Definitions

As used herein, the following terms have the following meanings:

The term "cyanoacrylate ester compositions" or "cyanoacrylate compositions" refers to polymerizable formulations comprising polymerizable cyanoacrylate ester monomers and/or oligomers which, in their monomeric form, are preferably compounds represented by formula I as described above.

More preferably, in formula I, R is an alkyl group of from 2 to 10 carbon atoms including, by way of example, ethyl, n-propyl, iso-propyl, n-butyl, iso-butyl, sec-butyl, n-pentyl, iso-pentyl, n-hexyl, iso-hexyl, 2-ethylhexyl, n-heptyl, n-octyl, nonyl, and decyl. More preferably, R is butyl, pentyl or octyl and most preferably, R is n-butyl. Mixtures of such compounds can also be employed.

Polymerizable cyanoacrylate esters are known in the art and are described in, for example, U.S. Pat. Nos. 3,527,224; 3,591,676; 3,667,472; 3,995,641; 4,035,334; and 4,650,826[1,2,7-10], the disclosures of each are incorporated herein by reference in their entirety.

A particularly preferred cyanoacrylate ester for use in the invention is n-butyl-2-cyanoacrylate.

The polymerizable cyanoacrylate ester compositions described herein rapidly polymerize in the presence of water vapor or tissue protein, and these prepolymers bond human skin tissue without causing histotoxicity or cytotoxicity.

Such polymerizable cyanoacrylate esters are sometimes referred to herein as prepolymers and compositions comprising such esters are sometimes referred to herein as prepolymer compositions.

The term "a biocompatible polymer" refers to polymers which, as iodine complexes (adducts), are compatible with in vivo applications of cyanoacrylate ester compositions onto mammalian skin including human skin. Representative polymers include polyvinylpyrrolidone, copolymers comprising polyvinylpyrrolidone which are optionally crosslinked, and the like. Suitable copolymers include copolymers of polyvinylpyrrolidone and vinyl acetate or other vinyl compounds which copolymers are optionally crosslinked with a polyisocyanate. The molecular weight of these polymers is not critical with number average molecular weights ranging from about 10,000 to about 1,000,000 and preferably from 30,000 to 300,000.

The term "a complex of iodine molecules with a biocompatible polymer" refers to an antimicrobial complex formed by the addition of iodine ($I_2$) to the biocompatible polymer. Such complexes are well known in the art and the resulting complex typically comprises both available iodine and iodide anions. These complexes, on contact with mammalian skin, are antimicrobial apparently by providing for a source of antimicrobial iodine. In any event, such complexes are employed only as starting materials herein and, by themselves, do not form a part of this invention.

These complexes are sometimes referred to herein simply by the term "iodine/polymer complexes". Such iodine/polymer complexes are distinguished from antibiotics which are naturally derived materials from either bacteria or fungi and whose mode of action is to interfere with bacterial processes resulting in bacterial death. Contrarily, the complexes used in this invention are indiscriminate in destroying any microbes including fungi, viruses and bacteria apparently by release of iodine into the microbes and, accordingly, are properly referred to as antimicrobial agents. Surprising, it has been found that iodine/polymer complexes are compatible in cyanoacrylate compositions. In fact, elemental (solid) iodine is incompatible with cyanoacrylate compositions because the addition of elemental iodine renders such compositions non-polymerizable on mammalian skin. Accordingly, complexation of the iodine with the biocompatible polymer is apparently essential for compatibility with the cyanoacrylate composition.

One preferred iodine/polymer complex for use in the compositions of this invention is either polyvinylpyrrolidone iodine complex which is described in, for example, the Tenth Edition of the Merck Index, Published by Merck & Co., Rahway, N.J., USA (1983). This complex is commercially available under the name "povidone-iodine" from BASF, Mt. Olive, N.J., USA.

Other suitable antimicrobial agents include complexes of iodine molecules with poloxamers or copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone and the like.

The term "biocompatible plasticizer" refers to any material which is soluble or dispersible in the cyanoacrylate composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127[17] and 4,444,933[18] the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. The particular biocompatible plasticizer employed is not critical and preferred plasticizers include dioctylphthalate and acetyl tri-n-butyl citrate.

The term "polymerization inhibitor" refers to mixtures of conventional acid polymerization inhibitors and free radical inhibitors of cyanoacrylate esters including materials such as mixtures comprising a first inhibitor such as sulfur dioxide, glacial acetic acid, C2–C6 organic acids, and the like and a second inhibitor such as hydroquinone and hindered phenols. The polymerization inhibitor is typically employed in amounts effective to inhibit polymerization until application onto mammalian skin.

Because of its compatibility with topical skin applications, the acid polymerization inhibitor is preferably sulfur dioxide which is preferably employed at from about 50 to 1000 ppm, more preferably from about 50 to 500 ppm and even more preferably 100 to 300 ppm, based on the total weight of the composition. Other preferred acid polymerization inhibitors include glacial acetic acid and other organic acids (e.g., $C_2$ to $C_6$ organic acids). Preferred free radical inhibitors include hydroquinone which is preferably employed at from about 50 to 500 ppm. Other free radical inhibitors include hindered phenols such as 4-methoxyphenol, 2,6-di-tert-butylphenol, and the like.

The term "antimicrobial agent" refers to agents which destroy microbes (i.e., bacteria, fungi, viruses and microbial spores) thereby preventing their development and pathogenic action.

The term "sanitizing agent" refers to any agent compatible with the packaging elements which, when contacted with these elements, sanitizes the package by reducing bioburden thereon. Preferably, bioburden is reduced to levels of less than about 10 colony forming units (CFU) on individual packaging elements and more preferably less than about 3 CFUs. Preferred sanitizing agents include, for example, heat, plasma and ethylene oxide. Other suitable sanitizing agents are well known in the art.

The term "visible light" refers to light having wavelengths of from about 200 to 780 nm, and preferably, 390 to 780 nm.

The term "transparent to visible light irradiation" refers to packaging elements which permit sufficient visible light irradiation to pass through the packaging element to sterilize polymerizable cyanoacrylate compositions contained therein. Preferably, the packaging element will permit at least about 50% of the visible light irradiation incident to the surface of the packaging element to traverse through the element; more preferably, at least 70% and still more preferably at least 80%.

Methods

The methods of this invention involve visible light sterilization of polymerizable cyanoacrylate compositions. In a preferred embodiment, the cyanoacrylate composition is first packaged into a suitable visible light transparent container which is preferably air-tight and moisture resistant. Such containers include, for example, glass, polyalkylene based polymers such as polypropylene or polyethylene, and the like. One suitable packaging element is described by Askill, et al.[15] Another suitable packaging element includes ampules made of polyolefins, fluorinated polyolefins and similar materials. Such materials possess low water vapor transmission and are inert to the cyanoacrylate ester.

In a preferred embodiment, the packaging element comprises high density polyethylene ampules having capacity of from about 0.3 to 10 mL of cyanoacrylate composition and a wall thickness of at least about 1 millimeter. In another preferred embodiment, polyolefin lined with a layer of silica is used as the packaging material because of its improved barrier properties and anticipated longer shelf life.

The packaging element is then filled to the desired level with a polymerizable cyanoacrylate ester composition using peristaltic or displacement pumps which are non-reactive with the cyanoacrylate composition. Filling of the packaging element employs any of several well known filling methods and the particular filling method is not critical to this invention and does not form part of the claimed invention. Once filled, the packaging elements are preferably sealed, again by conventional means. If necessary, the sealing means can include auxiliary sealing means. For example, an ampule comprising a screw cap sealing means can be further sealed by placement of a removable clear polymer coated film over the mouth of the ampule to which the screw cap overlays. Again, any conventional sealing means can be used as the sealing means does not form any part of this invention.

In one preferred embodiment, the ampule is open at one end prior to fill and subsequent to filling with the cyanoacrylate composition, the open terminus is compressed and heated sealed to effect closure.

In a particularly preferred embodiment, the ampule is subjected to a second packaging element such a polyfoil package or bag and then heated sealed to form a unitary packaging element for the ampule. Other secondary packaging elements which are water vapor resistant may employ form fill seal packaging equipment. The unitary packaging elements are then preferably boxed into groups or sets of elements which boxes are then subjected to visible light sterilization.

The packaging element, whether an individual element or individual elements combined by into larger packaging elements, is subjected to visible light sterilization. The visible light generator is any conventional generator of sufficient power and breadth of wavelength to effect sterilization. However, preferred generators are commercially available under the tradename PureBright® in-line sterilization systems from PurePulse Technologies, Inc. 4241 Ponderosa Ave, San Diego, Calif. 92123, USA.

The PureBright® in-line sterilization system employs visible light to sterilize clear liquids at an intensity approximately 90000 times greater than surface sunlight. Surprisingly, not withstanding the presence of UV radiation in the irradiation employed therein, it is contemplated that the methods of this invention will not result in significant polymerization of the cyanoacrylate composition.

If the amount of UV light penetration into the packaging element is of concern, the packaging element can incorporate a conventional UV absorber and/or the cyanoacrylate composition can be formulated with higher concentrations of stabilizers.

The dose of visible light irradiation employed is one sufficient to sterilize the packaging element as well as its contents. In a preferred embodiment, the visible light dosage is preferably from about 0.01 to 50 joules/square centimeter and more preferably from about 0.05 to about 5 joules/square centimeter with the specific dosage being selected relative to the density of material being subjected to visible light irradiation as well as the amount of bioburden estimated to be therein. Such factors are well within the skill of the art. Upon completion of the sterilization process, the sterilized product is ready for shipment to the ultimate user.

Visible light sterilization is preferably conducted at ambient atmospheric conditions such as a temperature of from about 15° C. to about 30° C. and the exposure time of the product to visible light irradiation is dependent on the fluence of the radiation employed and the dosage required which is well within the skill of the art. Preferably, exposure of the product to the visible light irradiation is less than 60 seconds. See, for instance, Clark, U.S. Pat. No. 5,925,885 which is incorporated herein by reference in its entirety.

In a particularly preferred embodiment, sterilization of the cyanoacrylate composition is facilitated by employing steps to reduce biocontamination of the packaging element and/or the cyanoacrylate composition prior to visible light irradiation sterilization. For example, the packaging element can be contacted with compatible sterilization or sanitization conditions prior to fill to reduce bioburden thereon. Since these sterilization or sanitization conditions are employed prior to incorporation of the cyanoacrylate composition, sterilization or sanitization conditions which are compatible with the packaging but would be otherwise incompatible with cyanoacrylate esters can be used including, for example, steam sterilization, heat sterilization, gas treatment, etc.

Likewise, the cyanoacrylate composition is preferably but optionally filtered with a small pore filter (<1 micron pore size) prior to addition to the packaging element. Filtration through, for example, 0.22 micron filter effectively reduces microbial contamination in the cyanoacrylate composition.

Using such steps prior to irradiation with visible light effectively reduces the dosage necessary to sterilize the composition.

In a particular embodiment, a primary packaging element such as a polyethylene ampule constructed for closure by heat sealing is sanitized by contacting the ampule with ethylene oxide under conventional conditions which reduce the bioburden to approximately zero.

Next, a polymerizable cyanoacrylate composition is filtered through a small pore filter such as a 0.22 micron filter which comprises material inert to the cyanoacrylate esters such as Telfon® filters. The filtered material is added to the sanitized ampule which is then heat sealed. Preferably, filtration, addition and sealing are done in a Class 100,000 or better clean room. The cyanoacrylate composition employed in the methods described herein is preferably fully formulated and more preferably contains cyanoacrylate ester prepolymer and polymerization inhibitors and, in some embodiments, a plasticizer and/or an antimicrobial agent such as povidone iodine.

Alternatively, the packaging element can contain the antimicrobial agent as a separate component thereof such that a 2 component system is provided which, at time of use, can be combined to provide for a single composition. See, for example, Lee, et al., U.S. Pat. No. 6,090,397 issued on Jul. 18, 2000 which patent is incorporated herein by reference in its entirety.

The primary packaging elements in the form of clear ampules can then be loaded into a secondary packaging element, such as a clear plastic.

In a final step, the packaged product is then subjected to sterilization by exposure to visible light irradiation.

The methods of this invention are particularly useful insofar as visible light sterilization does not result in solidification or gelation of the cyanoacrylate ester composition. Rather, the sterilized composition is liquid and retains its polymerizable properties. If necessary, solidification and/or gelation of the polymerizable cyanoacrylate ester composition can be further retarded by the use of polymerization inhibitors.

Compositions

The cyanoacrylate compositions used in the methods of this invention are prepared by conventional techniques of mixing the appropriate components until homogenous.

The specific viscosity of these compositions depends, in part, on the intended application of the composition. For example, relatively low viscosities are often preferred where application is to be made to a large surface area (e.g., abdominal surfaces). This preference results from the fact that those forms are less viscous and, accordingly, will permit more facile large surface area application of a thin film. Contrarily, where application is to be made to a specific position on the skin (e.g., elbow surfaces, knee surfaces and the like), higher viscosity compositions, including those containing thixotropic materials, are preferred to prevent "running" of the compositions to unintended locations.

Accordingly, these compositions have a viscosity of from about 2 to 50,000 centipoise at 20° C. Preferably the less viscous compositions have a viscosity of from about 2 to 1,500 centipoise at 20° C. More preferably, the cyanoacrylate ester employed in these compositions is almost entirely in monomeric form and the composition has a viscosity of from about 2 to about 100 centipoise at 20° C.

A thickening agent is optionally employed to increase the viscosity of the composition, which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like with PMMA being preferred. Fumed silica is particularly useful in producing a gel for topical application having a viscosity of from about 1500 to 50,000 centipoise at 20° C. Suitable thickening agents for the compositions described herein also include a partial polymer of the alkyl cyanoacrylate as disclosed in U.S. Pat. Nos. 3,654,239[3] and 4,038,345[16] both of which are incorporated herein by reference in their entirety.

Thickening agents are deemed to be biocompatible if they are soluble or dispersible in the composition and are compatible with the skin as measured by the lack of moderate to severe skin irritation.

Alternatively, the sterilization conditions can be selected such that the cyanoacrylate ester undergoes partial polymerization to reactive oligomers having a higher viscosity.

The cyanoacrylate compositions preferably include a biocompatible plasticizer and such plasticizers are preferably included in the composition from about 10 to 30 weight percent and more preferably from about 18 to 25 weight percent based on the total weight of the composition.

Additionally, the cyanoacrylate compositions described herein preferably include a mixture of polymerization inhibitors in an effective amount to inhibit premature polymerization of the composition during storage. Preferred mixtures of polymerization inhibitors are described above.

The polymerizable cyanoacrylate ester compositions may additionally contain one or more optional additives such as colorants, perfumes, rubber modifiers, modifying agents, etc. In practice, each of these optional additives should be both miscible and compatible with the cyanoacrylate composition and the resulting polymer. Compatible additives are those that do not prevent the use of the cyanoacrylates in the manner described herein.

In general, colorants are added so that the polymer layer formed on the skin will contain a discrete and discernable color. Perfumes are added to provide a pleasant smell to the formulation. Rubber modifiers are added to further enhance the flexibility of the resulting polymer layer. The amount of each of these optional additives employed in the composition is an amount necessary to achieve the desired effect.

Preferred cyanoacrylate compositions useful in the practice of this invention are also disclosed by Greff, et al.[14] which is incorporated herein by reference in its entirety.

In a particularly preferred embodiment, the cyanoacrylate composition further comprises an antimicrobially effective amount of a compatible antimicrobial agent. Such compositions preferably comprise from about 1 to about 30 and more preferably 3 to 20 weight percent of the compatible antimicrobial agent either as a solution or as a suspension based on the total weight of the composition. Compatible antimicrobial agents are those which are either soluble or suspendable in the cyanoacrylate composition, which do not cause premature polymerization of the cyanoacrylate composition, which do not prevent polymerization of the cyanoacrylate composition when applied to mammalian skin, and which are compatible with the intended use including biocompatibility with the patient's skin.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidone polymer which, when complexed with iodine, is also referred to under the common name of povidone-iodine available from BASF, Mt. Olive, N.J., USA. When povidone-iodine is employed in the cyanoacrylate composition, the composition preferably comprises from about 1 to about 30 weight percent and more preferably from about 3 to 20 weight percent of povidone-iodine based on the total weight of the composition.

Cyanoacrylate compositions comprising, for example, povidone-iodine are described by Greff, et al.[19], U.S. Pat. No. 5,684,042 which patent is incorporated herein by reference in its entirety.

Other suitable antimicrobial agents include complexes of iodine molecules with poloxamers or copolymers of vinylpyrrolidone and vinyl acetate, copolymers of vinylpyrrolidone and vinyl acetate cross-linked with polyisocyanates, copolymers of vinylpyrrolidone and vinyl functionalities, polymers of pyrrolidone and the like.

The use of a compatible antimicrobial agent in the composition permits the agent to be released from the polymeric film formed on mammalian skin thereby inhibiting microbial growth under this film. Additionally, since the film is maintained on mammalian skin for 1–4 days after formation, the release of antimicrobial agent further provides long term anti-infection benefits.

Utility

The methods of this invention are useful in providing sterilized cyanoacrylate compositions which can then be used for topical application to mammalian skin with reduced risk of introducing microbes onto the skin and, accordingly, reduced risk of infection. This is particularly important where topical application is onto skin areas which are already broken (e.g., small topical skin wounds or closing the surgical incision site) or which will become broken (e.g., application to form a surgical incise drape which will then be broken by the incision initiating the surgery).

The following example illustrates certain embodiments of the invention but are not meant to limit the scope of the claims in any way.

EXAMPLE

The following examples illustrate how the methods of this invention can be practiced. In these examples, all temperatures are in degrees Celsius (unless otherwise indicated) and all percents are weight percent (also unless otherwise indicated). Additionally, the following abbreviations have the following meanings. If an abbreviation is not defined, it has its generally accepted meaning.

g=gram mL=milliliter ppm=parts per million

Example 1

A two component skin prep is manufactured by placing 0.7 mL of n-butyl cyanoacrylate containing 500 ppm hydroquinone stabilizer, into a borosilicate glass ampoule which is then sealed with a gas flame. 40 sealed ampoules are placed in a PurePulse™ sterilizing apparatus that is part of the production line, and sterilized. The ampoules are then assembled into a dual chamber device such as described in U.S. Provisional Patent Application Serial No. 60/218979 (which is incorporated herein by reference in its entirety) with the ability to deliver a povidone iodine solution from one end and then cover it with a sealing coat of n-butyl cyanoacrylate delivered from the other end. The completed assembly is then incorporated into a procedure kit for use in an Operating Room, and the whole kit is sterilized using ethylene oxide gas.

Example 2

LiquiSeal™, a polymerizable cyanoacrylate composition comprising n-butyl cyanoacrylate, is prepared by filling an injection molded high density polyethylene ampoule coated on the inner surface with a layer of silica, with 0.5 g of monomer formulation. The formulation consists of 1000 ppm hydroquinone and 1000 ppm of 4-methoxy phenol in an 80:20 mixture of n-butyl cyanoacrylate and diethylhexyl phthalate. The ampoule is heat sealed an packaged immediately with an application brush into a thin film polypropylene sleeve with inner silica coating. Ten of these assemblies are then placed in the PurePulse™ sterilization equipment and the product sterilized.

From the foregoing description, various modifications and changes in the composition and method will occur to those skilled in the art. All such modifications coming within the scope of the appended claims are intended to be included therein.

What is claimed is:

1. A method for preparing a polymerizable, sterile, cyanoacrylate ester composition wherein the method comprises exposing a polymerizable cyanoacrylate ester composition to a predetermined dosage of visible light irradiation having wavelengths of from 390 to 780 nanometers wherein the predetermined dosage of visible light irradiation is sufficient to sterilize the polymerizable cyanoacrylate ester composition without gelling the polymerizable cyanoacrylate ester composition and is from about 0.01 to 50 joules/square centimeter.

2. The method according to claim 1 wherein the polymerizable cyanoacrylate ester is a polymerizable monomer or oligomer of a cyanoacrylate ester which, in monomeric form, is represented by formula I:

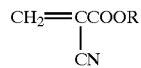

I wherein R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

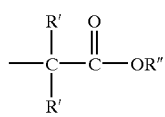

wherein each R' is independently selected from the group consisting of:

hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

3. The method according to claim 2 wherein R is alkyl of from 4 to 10 carbon atoms.

4. The method according to claim 3 wherein R is alkyl of from 4 to 8 carbon atoms.

5. The method according to claim 4 wherein R is selected from the group consisting of butyl, pentyl or octyl.

6. The method according to claim 5 wherein R is n-butyl.

7. The method according to claim 1 wherein the cyanoacrylate composition further comprises a complex of iodine molecules with a biocompatible polymer.

8. The method according to claim 1 wherein the cyanoacrylate composition further comprises a biocompatible plasticizer.

9. The method according to claim 8 wherein said biocompatible plasticizer is selected from the group consisting of dioctyl phthalate and acetyl tri-n-butyl citrate.

10. The method according to claim 1 wherein the cyanoacrylate composition further comprises a polymerization inhibitor.

11. The method according to claim 10 wherein said polymerization inhibitor is $SO_2$.

12. A method for preparing a polymerizable, sterile, cyanoacrylate ester composition in a packaging element wherein the method comprises:
(a) selecting a packaging element which is transparent to visible light irradiation;
(b) adding a polymerizable cyanoacrylate ester composition to the packaging element selected in (a) above; and
(c) exposing the packaging element formed in (b) above to a predetermined dosage of visible light irradiation having wavelengths of from 390 to 780 nanometers wherein the predetermined dosage of visible light irradiation is sufficient to sterilize both the packaging element and the polymerizable cyanoacrylate ester composition therein without gelling the polymerizable cyanoacrylate ester composition and is from about 0.01 to 50 joules/square centimeter.

13. A method for preparing a polymerizable, sterile, cyanoacrylate ester composition in a packaging element wherein the method comprises:
(a) selecting a packaging element in the form of an ampule having a neck portion configured for heat sealing after fill wherein said packaging element is transparent to visible light irradiation;
(b) exposing said ampule to a sufficient amount of a sanitizing agent to reduce the level of bioburden on the ampule;
(c) selecting a polymerizable cyanoacrylate ester composition;
(d) filtering said polymerizable cyanoacrylate ester composition through a biofilter having a maximum pore size of less than about 1 micron;
(e) adding the filtered polymerizable cyanoacrylate ester composition to the ampule prepared in (b) above;

(f) sealing the ampule prepared in (e) by heat sealing the neck portion of said ampule;

(g) combining ampules produced in (f) above into a set of ampules;

(h) sealing the set of ampules formed in (g) above with a secondary sealing means so as to form a packaging element comprising said set of ampules; and (i) exposing the packaging element formed in (h) above to a predetermined dosage of visible light having wavelengths of from 390 to 780 nanometers wherein the predetermined dosage of visible light irradiation is sufficient to sterilize both the packaging element and the polymerizable cyanoacrylate ester composition therein without solidifying or gelling the composition and is from about 0.01 to 50 joules/square centimeter.

14. The method of claim 13 wherein the polymerizable cyanoacrylate ester is a polymerizable monomer or oligomer of a cyanoacrylate ester which, in monomeric form, is n-butyl cyanoacrylate.

15. The method of claims 1, 12 or 13 wherein the predetermined dosage of visible light irradiation is from about 0.05 to 5 joules/square centimeter.

* * * * *